US009266826B2

(12) United States Patent
Hamase et al.

(10) Patent No.: US 9,266,826 B2
(45) Date of Patent: Feb. 23, 2016

(54) SEPARATING AGENT AND MANUFACTURING METHOD THEREOF

(71) Applicants: SHISEIDO COMPANY, LTD., Tokyo (JP); KYUSHU UNIVERSITY, NATIONAL UNIVERSITY CORPORATION, Fukuoka (JP)

(72) Inventors: Kenji Hamase, Fukuoka (JP); Masashi Mita, Tokyo (JP); Yousuke Toujo, Kanagawa (JP); Yukimitsu Suda, Tokyo (JP)

(73) Assignees: SHISEIDO COMPANY, LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/374,569

(22) PCT Filed: Jan. 31, 2013

(86) PCT No.: PCT/JP2013/052256
§ 371 (c)(1),
(2) Date: Jul. 25, 2014

(87) PCT Pub. No.: WO2013/115334
PCT Pub. Date: Aug. 8, 2013

(65) Prior Publication Data
US 2014/0378705 A1    Dec. 25, 2014

(30) Foreign Application Priority Data

Jan. 31, 2012  (JP) .................................. 2012-018838

(51) Int. Cl.
*C07C 275/30*  (2006.01)
*B01J 20/288*  (2006.01)
*B01J 20/32*  (2006.01)
*C07C 273/18*  (2006.01)
*B01J 20/29*  (2006.01)
*B01D 15/38*  (2006.01)

(52) U.S. Cl.
CPC .......... *C07C 275/30* (2013.01); *B01D 15/3833* (2013.01); *B01J 20/288* (2013.01); *B01J 20/29* (2013.01); *B01J 20/3204* (2013.01); *B01J 20/3219* (2013.01); *B01J 20/3244* (2013.01); *B01J 20/3253* (2013.01); *B01J 20/3293* (2013.01); *C07C 273/1854* (2013.01); *B01J 2220/4812* (2013.01); *B01J 2220/80* (2013.01); *C07B 2200/07* (2013.01)

(58) Field of Classification Search
CPC ........ B01J 20/22; B01J 20/281; B01J 20/288; B01J 20/30; B01J 20/3244; B01J 2220/4812; B01J 2220/80; C07B 2200/07; C07C 273/1854; C07C 275/30
USPC .......................................................... 564/50
See application file for complete search history.

(56) References Cited

U.S. PATENT DOCUMENTS

| 5,338,529 A | 8/1994 | Pirkle et al. |
| 5,487,831 A | 1/1996 | Pirkle et al. |

FOREIGN PATENT DOCUMENTS

| JP | S64-54379 | 3/1989 |
| JP | S64-54380 | 3/1989 |
| JP | S64-54381 | 3/1989 |
| JP | 2000-74896 | 3/2000 |
| JP | 2005-3558 | 1/2005 |
| JP | 2009-31049 | 2/2009 |
| WO | 93/22272 | 11/1993 |

OTHER PUBLICATIONS

Fuentes ("Chiral recognition with a benzofuran receptor that mimics an oxyanion hole" Organic and Biomolecular Chemistry, 2015, 13, p. 493-501).* Hamase ("Enantioselective Determination of Extraterrestrial Amino Acids Using a Two-Dimensional Chiral High-Performance Liquid Chromatographic System" Chromatography, 2014, 35, p. 103-110).*

Machine translation of JP2000-074896, 1-4 pages, obtained on Jun. 29, 2015.*
International Search Report mailed on Apr. 2, 2013.
Naobumi Oi et al., Direct separation of carboxylic acid enantiomers by high-performance liquid chromatography with amide and urea derivatives bonded to silica gel as chiral stationary phases, Journal of Chromatography A, Jan. 13, 1995, vol. 689, Issue 2, pp. 195-201.
M. Muller et al., Plasma aminofunctionalisation of PVDF microfiltration membranes: comparison of the in plasma modifications with a grafting method using ESCA and an amino-selective fluorescent probe, Surface and Coatings Technology, 116-119 (1999) 802-807.
Lidija Tusek et al., Surface characterisation of NH3 plasma treated polyamide 6 foils, Colloids and Surfaces A: Physicochemical and Engineering Aspects, 195 (2001) 81-95.
Fabienne Poncin-Epaillard et al., Reactivity of surface groups formed onto a plasma treated poly(propylene) film, Macromol. Chem. Phys., 200, 989-996 (1999).
"Determination of D-amino Acids by Improved Pirkle-type Chiral Stationary Phases", [online], Sumika Chemical Analysis Service Limited, Technical News, TN257, [retrieval on Heisei 24 (2012) Jan. 28], Internet <URL:http://www.scas.co.jp/analysis/pdf/tn257.pdf>.
Extended European Search Report dated Oct. 28, 2015.
Anonymous, "Regis Technologies Chromatography Catalog", Aug. 13, 2011, pp. 1-64, KP055221263, Morton Grove, IL Retrieved from the Internet: URL:https://web.archive.org/web/20110813201755/ http://www.registech.com/Library/Catalog/RegisCatalog.pdf [retrieved on Oct. 15, 2015].

\* cited by examiner

*Primary Examiner* — Jafar Parsa
*Assistant Examiner* — Amy C Bonaparte
(74) *Attorney, Agent, or Firm* — IPUSA, PLLC

(57) ABSTRACT

An embodiment of the present invention is a separating agent wherein a group represented by a chemical formula of:

[Chem. 1]

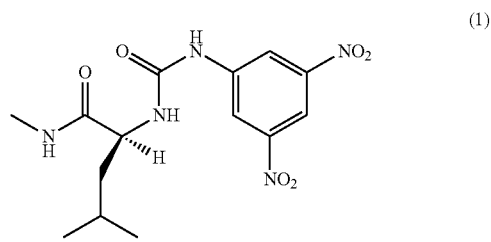

(1)

or a group represented by a chemical formula of:

[Chem. 2]

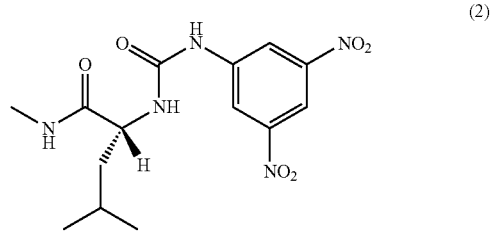

(2)

is introduced on a surface thereof.

7 Claims, 4 Drawing Sheets

SEPARATING AGENT AND MANUFACTURING METHOD THEREOF

TECHNICAL FIELD

An embodiment of the present invention relates to a separating agent, a manufacturing method of a separating agent, a column, a liquid chromatograph, a separation method, and a compound.

BACKGROUND ART

In recent years, the presence of various enantiomers has been confirmed within the bodies of higher order animals such as mammals, and the important functions that each enantiomer serves are being elucidated. Among amino acids, large amounts of L-amino acids are present inside a body as constituents of proteins or nutrient sources whereas trace amounts of D-amino acids that are enantiomers thereof are frequently present inside the body. Because of this, when D-amino acids are analyzed, interference from a wide variety of peptides or amino compounds frequently occurs. Furthermore, mass spectrometry used for analysis at a high resolution is such that separation of enantiomers is impossible in principle, and hence, development of an optical resolution technique at a high resolution is desired to conduct accurate quantitative analysis.

Non-Patent Document 1 discloses a method for optically resolving fluorescently derivatized amino acids by using SUMICHIRAL (registered trademark) OA2500S (produced by Sumika Chemical Analysis Service, Ltd.).

Patent Document 1 discloses a two-dimensional HPLC wherein a column for optical resolution is combined with a reversed-phase column.

However, in addition to the elution order of D-bodies and L-bodies of amino acids not being identical, there is a problem of a low resolution between peaks originating from the D-bodies and peaks originating from the L-bodies.

PRIOR ART DOCUMENTS

Patent Documents

Patent Document 1: Japanese Laid-Open Patent Application No. 2005-3558 official gazette.

Non-Patent Documents

Non-Patent Document 1: "A method of measurement of D-amino acids on a Pirkle improved column", [online], Sumika Chemical Analysis Service Limited, Technical News, TN257, [retrieval on Heisei 24 (2012 Jan. 28)], Internet <URL:http://www.scas.co.jp/analysis/pdf/tn257.pdf>.

SUMMARY OF THE INVENTION

Problems to be Solved by the Invention

While a problem possessed by the conventional technique described above is taken into consideration, an embodiment of the present invention aims at providing a separating agent capable of causing the elution order of D-bodies and L-bodies of an amino acid to be identical and improving resolutions between peaks originating from the D-bodies and peaks originating from the L-bodies, and a compound capable of manufacturing the separating agent.

Means for Solving the Problem

An embodiment of the present invention is a separating agent wherein a group represented by a chemical formula of:

[Chem. 1]

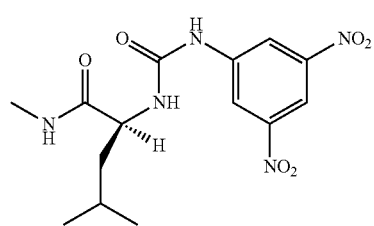

(1)

or a group represented by a chemical formula of:

[Chem. 2]

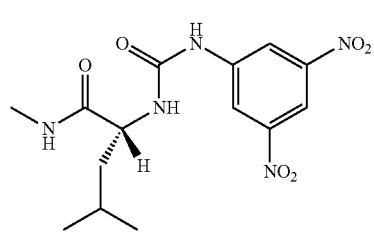

(2)

is introduced on a surface thereof.

An embodiment of the present invention is a manufacturing method of a separating agent, which has a step of condensing a compound represented by a chemical formula of:

[Chem. 3]

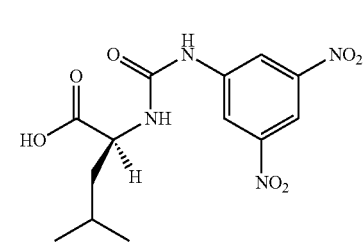

(3)

or a compound represented by a chemical formula of:

[Chem. 4]

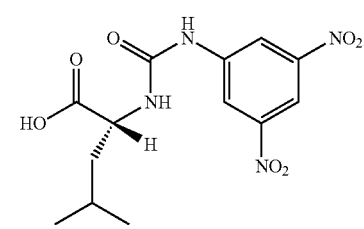

(4)

with a substrate with an amino group being present on a surface thereof.

An embodiment of the present invention is a compound represented by a chemical formula of:

[Chem. 5]

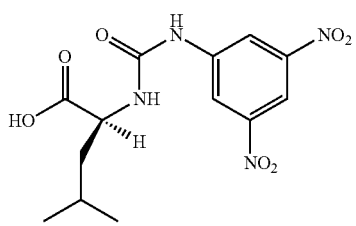
(3)

or a chemical formula of:

[Chem. 6]

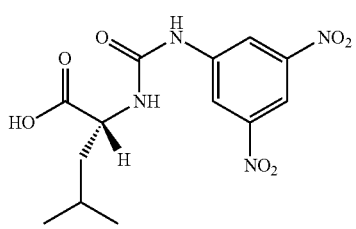
(4)

Effects of the Invention

According to an embodiment of the present invention, it is possible to provide a separating agent capable of causing the elution order of D-bodies and L-bodies of amino acids to be identical and improving resolutions between peaks originating from the D-bodies and peaks originating from the L-bodies, and a compound capable of manufacturing the separating agent.

EMBODIMENTS FOR IMPLEMENTING THE INVENTION

Figure 1:
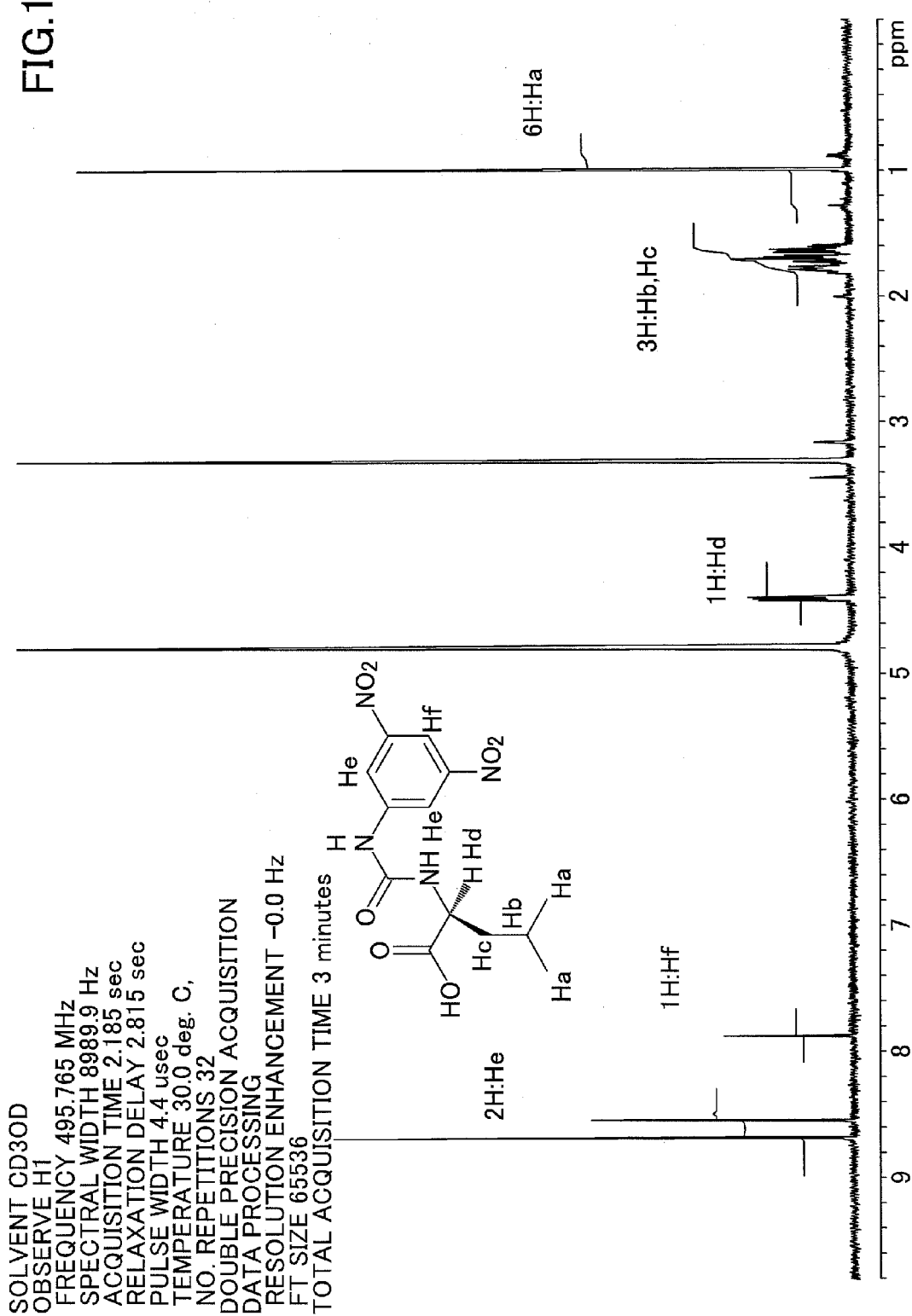
[FIG. 1] is a $^1$H NMR spectrum of a compound represented by chemical formula (3).

Next, an embodiment of the present invention will be described in conjunction with the drawings.

A separating agent is such that a group represented by chemical formula (1) or a group represented by chemical formula (2) is introduced on a surface thereof. Accordingly, it is possible to cause the elution order of D-bodies and L-bodies of amino acids to be identical and to improve resolutions between peaks originating from the D-bodies and peaks originating from the L-bodies.

A shape of a separating agent is not particularly limited and it is possible to provide a filler, a continuous porous body, or the like.

It is possible to manufacture a separating agent by condensing a compound represented by chemical formula (3) or a compound represented by chemical formula (4) with a substrate with an amino group being present on a surface thereof.

As a compound represented by chemical formula (3) or a compound represented by chemical formula (4) is condensed with a substrate with an amino group being present on a surface thereof, an amide linkage is formed.

When a compound represented by chemical formula (3) or a compound represented by chemical formula (4) is condensed with a substrate with an amino group being present on a surface thereof, a condensing agent may be added thereto.

A condensing agent is not particularly limited and it is possible to provide a triazine-type condensing agent such as a 4-(4,6-dimethoxy-1,3,5-triazine-2-yl)-4-methylmorpholinium chloride, a carbodiimide-type condensing agent such as a 1-ethyl-3-(3-dimethylaminopropyl)carbodiimide hydrochloride, or the like.

Here, a separating agent may be manufactured by producing a carboxylic acid halide from a compound represented by chemical formula (3) or a compound represented by chemical formula (4) and subsequently reacting therewith a substrate with an amino group being present on a surface thereof.

A shape of a substrate with an amino group being present on a surface thereof is not particularly limited and it is possible to provide a particle, a continuous porous body, or the like.

An average particle diameter of a particle with an amino group being present on a surface thereof is usually 1-200 μm and 1-5 μm is preferable.

It is preferable for a particle with an amino group being present on a surface thereof to be a porous particle.

An average pore diameter of a porous particle with an amino group being present on a surface thereof is usually 1-50 nm and 8-30 nm is preferable.

A specific surface area of a porous particle with an amino group being present on a surface thereof is usually 50-800 m$^2$/g and 100-600 m$^2$/g is preferable.

For a commercial item of porous particles with an amino group being present on a surface thereof, it is possible to provide Mightysil NH$_2$ (produced by TOSOH CORPORATION).

It is possible to manufacture a substrate with an amino group being present on a surface thereof by introducing an amino group onto a surface of a substrate.

A material that composes a substrate capable of introducing an amino group onto a substrate thereof is not particularly limited and it is possible to provide a silica, a silica gel, an activated carbon, a zeolite, an alumina, a clay mineral, a poly(styrene), a styrene-divinylbenzene copolymer, a silicic acid compound, poly(methacrylic acid), a poly(hydroxymethacrylic acid), a poly(vinyl alcohol), a cellulose, an agarose, a dextrin, a xanthone, a hydroxyapatite, a zirconia, or the like.

A method for introducing an amino group onto a surface of a substrate is not particularly limited and it is possible to provide a method for nitrogen-plasma-treating a substrate, a method for ammonia-plasma-treating a substrate, a method for reacting a surface-treating agent with a substrate, a method for silicone-vapor-phase-treating a substrate, or the like.

In a method for nitrogen-plasma-treating a substrate, a low temperature plasma is generated under a nitrogen gas atmosphere and thereby an amino group is introduced onto a surface of a substrate (for example, see Surface and Coatings Technology 116-119 (1999) 802-807, Colloids and Surfaces A: Physicochem. Eng. Aspects 195 (2001) 81-95, Macromol. Chem. Phys. 200. 989-996 (1999)).

In a method for ammonia-plasma-treating a substrate, a low temperature plasma is generated under an ammonia gas atmosphere and thereby an amino group is introduced onto a surface of a substrate.

In a method for reacting a surface-treating agent with a substrate, a silane coupling agent such as an alkoxysilane, a chlorosilane, or a silazane, that has an amino group, is used to introduce an amino group onto a surface of a substrate with a group capable of producing a silanol group through hydrolysis thereof, a silanol group, a hydroxyl group originating from a semimetal oxide, and/or a hydroxyl group originating from a metal oxide being present on the surface.

In a method for silicone-vapor-phase-treating a substrate, a 1,3,5,7-tetramethylcyclotetrasiloxane is used to introduce a hydrosilyl group onto a surface of a substrate and subsequently an alkene that has an amino group is reacted therewith, thereby introducing such an amino group onto the surface of the substrate (for example, see Japanese Examined Patent Application No. 1-54379 official gazette, Japanese Examined Patent Application No. 1-54380 official gazette, and Japanese Examined Patent Application No. 1-54381 official gazette).

An alkene that has an amino group is not particularly limited and it is possible to provide an amine that has a vinyl group, an amine that has an acryl group, or the like.

Here, an amino group that is had by an alkene may be protected with a butoxycarbonyl group, a benzyloxycarbonyl group, or the like.

Furthermore, instead of an alkene that has an amino group, an alkene that has a group capable of introducing an amino group through a reaction with, for example, a diamine, such as an epoxy group, may be used.

An optical resolution column has the aforementioned separating agent wherein a filler may fill a tube or a continuous porous body may be fixed on a tube.

A material that composed a tube is not particularly limited and it is possible to provide a stainless steel, a resin, a glass, a quartz, or the like.

A liquid chromatograph has the aforementioned optical resolution column and it is preferable to further have a reversed phase column capable of separating an amino acid or an amino acid derivative (for example, see Patent Document 1). In this case, a reversed phase column is used to separate an amino acid or an amino acid derivative and subsequently an optical resolution column is used to separate between a D-body and an L-body of a separated amino acid or amino acid derivative, whereby it is possible to analyze contents of a D-amino acid and an L-amino acid in a biological sample at once.

Here, after a liquid chromatograph that has a reversed phase column capable of separating an amino acid or an amino acid derivative is used to fractionate an amino acid or amino acid derivative that is contained in a biological sample, a liquid chromatograph that has the aforementioned optical resolution column may be used to separate between a D-body and an L-body of a fractionated amino acid or amino acid derivative.

Furthermore, after a solid phase extraction method is used to extract an amino acid or an amino acid derivative that is contained in a biological sample, a liquid chromatograph that has the aforementioned optical resolution column may be used to separate between a D-body and an L-body of an extracted amino acid or amino acid derivative.

An amino acid is not particularly limited as long as an asymmetric carbon is had thereby, and it is possible to provide an alanine, a cysteine, an aspartic acid, a glutamic acid, a phenylalanine, a histidine, an isoleucine, a lysine, a leucine, a methionine, an asparagine, a proline, a glutamine, an arginine, a serine, a threonine, a valine, a tryptophan, a tyrosine, or the like.

A reagent used for synthesizing an amino acid derivative is not particularly limited and it is possible to provide a 4-fluoro-7-nitro-2,1,3-benzoxadiazole, an o-phthalaldehyde, a phenyl isothiocyanate, a fluorescamine, a dansyl chloride, or the like.

Here, it is also possible to apply the aforementioned separating agent, optical resolution column, and liquid chromatograph to separation of an enantiomer or a diastereomer other than an amino acid and an amino acid derivative.

PRACTICAL EXAMPLES

Practical Example 1

Synthesis of a Compound Represented by Chemical Formula (3)

520 mg of L-leucine, 420 mg of 3,5-dinitrophenylisocyanate, 5 mL of a 1 M aqueous solution of sodium hydroxide, and 1.5 mL of tetrahydrofuran were agitated at room temperature for 6 hours, and subsequently, 0.5 mL of a 1 M aqueous solution of sodium hydroxide were added thereto. Then, liquid separation with 6 mL of a mixed solvent of ethyl acetate/hexane with a volume ratio of 3:1 was conducted 3 times, and subsequently, 1.5 mL of 3 N hydrochloric acid was added to an aqueous phase. Moreover, liquid separation with 10 mL of ethyl acetate was conducted 4 times, and subsequently, liquid separation of an oil phase with 5 mL of a saturated aqueous solution of sodium chloride was conducted 1 time. Then, sodium sulfate was added to the oils phase to cause drying thereof, and subsequently, drying thereof was conducted by using an evaporator. Moreover, 2 mL of ethyl acetate were added thereto, and subsequently, hexane was added to cause recrystallization thereof, so that a coarse crystal was obtained. Then, 200 μL of methanol and 100 μL of 0.1% by mass of a hydrochloric acid aqueous solution were added to 150 mg of the coarse crystal, and subsequently fractionation thereof was conducted by using a high performance liquid chromatograph GULLIVER (produced by JASCO Corporation). Moreover, a fractionated fraction was dried by using an evaporator. Then, liquid separation with 35 mL of ethyl acetate was conducted 2 times, and subsequently, liquid separation of an oil phase with 5 mL of a saturated aqueous solution of sodium chloride was conducted 1 time. Then, sodium sulfate was added to the oil phase to cause drying thereof, and subsequently, drying thereof was conducted by using an evaporator. Moreover, 2 mL of ethyl acetate was added thereto, and subsequently, hexane was added to cause recrystallization thereof, so that a colorless needle crystal of a compound represented by chemical formula (3) was obtained.

Here, a compound represented by chemical formula (4) could be synthesized similarly to the compound represented by chemical formula (3) except that D-leucine was used instead of L-leucine.

[$^1$HNMR]

A $^1$HNMR spectrum of the compound represented by chemical formula (3) in deuterated methanol was measured by using Unity Plus 500 (produced by Varian Medical Systems, Inc.) (see FIG. 1).

[Chemical Purity]

As a chemical purity of the compound represented by chemical formula (3) was analyzed by using the $^1$HNMR spectrum in FIG. 1, 99% or higher was provided.

[Optical Purity]

As an optical purity of the compound represented by chemical formula (3) was analyzed by using a high performance liquid chromatograph NANOSPACE SI-2 (produced by Shiseido Co., Ltd.), 99.8% or higher was provided. Here, analysis conditions were as follows.

Column: SUMICHIRAL (registered trademark) OA-3200S (inner diameter: 1.5 mm, total length: 250 mm)

Temperature: 25° C.

Mobile phase: 0.2 mM solution of citric acid in methanol

Flow rate of the mobile phase: 200 µL/min

[Fabrication of Porous Spherical Silica Gel Particles with an Amino Group(s) being Present on a Surface Thereof]

10 g of porous spherical silica gel particles with an average particle diameter of 5 µm, an average pore diameter of 12.5 nm, and a specific surface area of 300 m$^2$/g were dispersed in a mixed solvent of 15 ml of water and 15 ml of 2-propanol, and subsequently, 5 g of 3-aminopropyltrimethoxysilane were added thereto. Then, temperature elevation to 85° C. was conducted to cause a reaction for 6 hours, and subsequently, filtration was conducted. Moreover, a filtered substance was washed with methanol and distilled water and subsequently dried to obtain porous spherical silica gel particles with an amino group(s) being present on a surface thereof.

[Fabrication of a Filler]

1.5 molar equivalents of 4-(4,6-dimethoxy-1,3,5-triazine-2-yl)-4-methylmorpholinium chloride with respect to the compound represented by chemical formula (3) were added to a solution with 0.7 g of the compound represented by chemical formula (3) being dissolved in 30 mL of water, and subsequently, agitation thereof was conducted at room temperature for 2 hours. Then, 1.25 g of the porous spherical silica gel particles with an amino group(s) being present on a surface thereof were added thereto, subsequently, reaction thereof was caused at room temperature overnight, and subsequently, filtration thereof was conducted. Moreover, a filtered substance was washed with methanol and chloroform and subsequently dried to obtain a filler.

[Fabrication of a Column]

A tube made of stainless steel with an inner diameter of 1.5 mm and a length of 250 mm was filled with the filler to fabricate a column.

[Separation Between the D-body and L-body of Arginine (Arg)]

20 µL of a 200 mM (pH 8.0) buffer solution of sodium borate with a pH of 8.0 and 5 µL of a 40 mM solution of 4-fluoro-7-nitro-2,1,3-benzoxadiazole in anhydrous methyl cyanide were added to 50 pmol of a mixture of the D-body and the L-body of Arginine with a mass ratio of 1:4, and subsequently, heating was conducted at 60° C. for 2 minutes to cause fluorescent derivatization thereof. Then, 95 µL of a 0.5% aqueous solution of trifluoroacetic acid was added thereto, so that a measurement sample was obtained.

The column was mounted on a high performance liquid chromatograph SI-2 (produced by Shiseido Co., Ltd.), and subsequently, 2 µL of the measurement sample was injected thereto on the following conditions, so that the D-body and the L-body of arginine were separated.

Temperature: 25° C.

Mobile phase: methanol

Flow rate of the mobile phase: 150 L/min

[Separation Between the D-body and the L-body of Histidine (His)]

The D-body and the L-body of histidine were separated similarly to the D-body and the L-body of arginine except that a 0.25 mM solution of citric acid in a mixed solvent of methanol/acetonitrile (volume ratio: 97.5/2.5) was used instead of methanol.

[Separation Between the D-body and the L-body of Proline (Pro)]

The D-body and the L-body of proline were separated similarly to the D-body and the L-body of arginine except that a 3 mM solution of citric acid in a mixed solvent of methanol/acetonitrile (volume ratio: 70/30) was used instead of methanol.

[Separation Between the D-body and the L-body of Alanine (Ala)]

The D-body and the L-body of alanine were separated similarly to the D-body and the L-body of arginine except that a 1 mM solution of citric acid in a mixed solvent of methanol/acetonitrile (volume ratio: 90/10) was used instead of methanol.

[Separation Between the D-body and the L-body of Valine (Val)]

The D-body and the L-body of valine were separated similarly to the D-body and the L-body of arginine except that a 1 mM solution of citric acid in a mixed solvent of methanol/acetonitrile (volume ratio: 90/10) was used instead of methanol.

[Separation Between the D-body and the L-body of Alloisoleucine (Allo-Ile)]

The D-body and the L-body of alloisoleucine were separated similarly to the D-body and the L-body of arginine except that a 1 mM solution of citric acid in a mixed solvent of methanol/acetonitrile (volume ratio: 90/10) was used instead of methanol.

[Separation Between the D-body and the L-body of Isoleucine (Ile)]

The D-body and the L-body of isoleucine were separated similarly to the D-body and the L-body of arginine except that a 1 mM solution of citric acid in a mixed solvent of methanol/acetonitrile (volume ratio: 90/10) was used instead of methanol.

[Separation Between the D-body and the L-body of Leucine (Leu)]

The D-body and the L-body of leucine were separated similarly to the D-body and the L-body of arginine except that a 1 mM solution of citric acid in a mixed solvent of methanol/acetonitrile (volume ratio: 90/10) was used instead of methanol.

[Separation Between the D-body and the L-body of Asparagine (Asn)]

The D-body and the L-body of asparagine were separated similarly to the D-body and the L-body of arginine except that a 2 mM solution of citric acid in a mixed solvent of methanol/acetonitrile (volume ratio: 80/20) was used instead of methanol.

[Separation Between the D-body and the L-body of Glutamine (Glu)]

The D-body and the L-body of glutamine at a mass ratio of 1:4 were separated similarly to the D-body and the L-body of arginine at a mass ratio of 1:4 except that a 2 mM solution of citric acid in a mixed solvent of methanol/acetonitrile (volume ratio: 80/20) was used instead of methanol.

[Separation Between the D-body and the L-body of Serine (Ser)]

The D-body and the L-body of serine were separated similarly to the D-body and the L-body of arginine except that a 1.5 mM solution of citric acid in a mixed solvent of methanol/acetonitrile (volume ratio: 85/15) was used instead of methanol.

[Separation Between the D-body and the L-body of Allothreonine (Allo-Thr)]

The D-body and the L-body of allothreonine were separated similarly to the D-body and the L-body of arginine except that a 1 mM solution of citric acid in a mixed solvent of methanol/acetonitrile (volume ratio: 90/10) was used instead of methanol.

[Separation Between the D-body and the L-body of Threonine (Thr)]

The D-body and the L-body of threonine were separated similarly to the D-body and the L-body of arginine except that a 2 mM solution of citric acid in a mixed solvent of methanol/acetonitrile (volume ratio: 80/20) was used instead of methanol.

[Separation Between the D-body and the L-body of Methionine (Met)]

The D-body and the L-body of methionine were separated similarly to the D-body and the L-body of arginine except that a 3 mM solution of citric acid in a mixed solvent of methanol/acetonitrile (volume ratio: 70/30) was used instead of methanol.

[Separation Between the D-body and the L-body of Phenylalanine (Phe)]

The D-body and the L-body of phenylalanine were separated similarly to the D-body and the L-body of arginine except that a 5 mM solution of citric acid in a mixed solvent of methanol/acetonitrile (volume ratio: 50/50) was used instead of methanol.

[Separation Between the D-body and the L-body of Lysine (Lys)]

The D-body and the L-body of lysine were separated similarly to the D-body and the L-body of arginine except that a 5 mM solution of citric acid in a mixed solvent of methanol/acetonitrile (volume ratio: 50/50) was used instead of methanol.

[Separation Between the D-body and the L-body of Aspartic Acid (Asp)]

The D-body and the L-body of aspartic acid were separated similarly to the D-body and the L-body of arginine except that a 5 mM solution of citric acid in a mixed solvent of methanol/acetonitrile (volume ratio: 50/50) was used instead of methanol.

[Separation Between the D-body and the L-body of Glutamic Acid (Glu)]

The D-body and the L-body of glutamic acid were separated similarly to the D-body and the L-body of arginine except that a 1.5 mM solution of citric acid in a mixed solvent of methanol/acetonitrile (volume ratio: 85/15) was used instead of methanol.

[Separation Between the D-body and the L-body of Cysteine (Cys)]

The D-body and the L-body of cysteine were separated similarly to the D-body and the L-body of arginine except that a 5 mM solution of citric acid in a mixed solvent of methanol/acetonitrile (volume ratio: 50/50) was used instead of methanol.

[Separation Between the D-body and the L-body of Tyrosine (Tyr)]

The D-body and the L-body of tyrosine were separated similarly to the D-body and the L-body of arginine except that a 3 mM solution of citric acid in a mixed solvent of methanol/acetonitrile (volume ratio: 70/30) was used instead of methanol.

[Separation Between the D-body and the L-body of Tryptophan (Trp)]

The D-body and the L-body of tryptophan were separated similarly to the D-body and the L-body of arginine except that a 1 mM solution of citric acid in a mixed solvent of methanol/acetonitrile (volume ratio: 90/10) was used instead of methanol.

Figure 2:
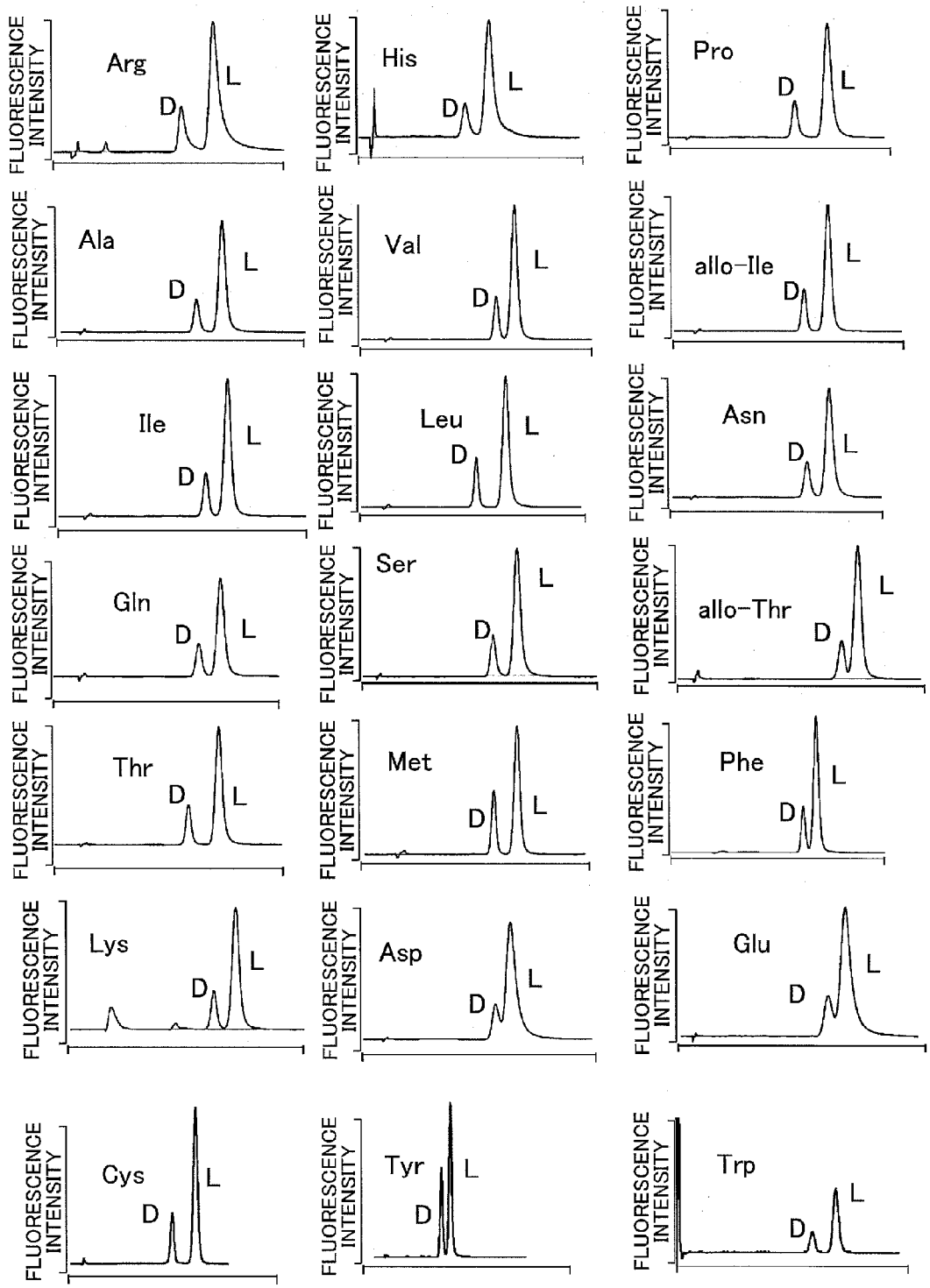
[FIG. 2] is chromatograms of amino acids in Practical Example 1.

FIG. 2 illustrates chromatograms of amino acids.

It was found from FIG. 2 that the D-bodies were eluted earlier than the L-bodies with respect to all the amino acids.

It was also found that resolutions of peaks originating from the D-bodies and peaks originating from the L-bodies were high with respect to all the amino acids because peak-to-valley ratios thereof were greater than or equal to 2.0 and symmetry coefficients thereof were less than 4.0.

[Peak-to-valley Ratio]

The peak-to-valley ratios were calculated from a formula of:

$$Hp/Hv$$

wherein Hp is a height of a peak originating from a D-body with respect to a baseline and Hv is a height at a point with a lowest height (a valley between peaks) between the peak originating from the D-body and a peak originating from an L-body with respect to the baseline (see Japanese Pharmacopoeia).

[Symmetry Coefficient]

The symmetry coefficients were calculated from a formula of:

$$S=W/(2\times F)$$

wherein W is a width of a peak at a height that is 1/10 of a height of the peak with respect to a baseline and F is a distance of the peak at a side of rising thereof when W is divided into two by a perpendicular going down from a top of the peak to a transverse axis on a recording paper sheet.

Here, although a width of a peak at a height that is 1/20 of a height of the peak with respect to a baseline is used as W in the Japanese Standards of Quasi-drug Ingredients, a width of a peak at a height that is 1/10 of a height of the peak with respect to a baseline was used as W because a valley of a peak of arginine (Arg) in Comparative Example 2 was present at a position higher than a height that was 1/20 of a height of the peak with respect to a baseline.

Comparative Example 1

Mixtures of the D-bodies and the L-bodies of amino acids at mass ratios of 1:4 were separated similarly to Practical Example 1 expect that SUMICHIRAL (registered trademark) OA-2500S (produced by SCAS, Ltd.) was used as a column. Here, an optically active component of SUMICHIRAL (registered trademark) OA-2500S (produced by SCAS, Ltd.) was (S)-1-naphthylglycine.

Figure 3:
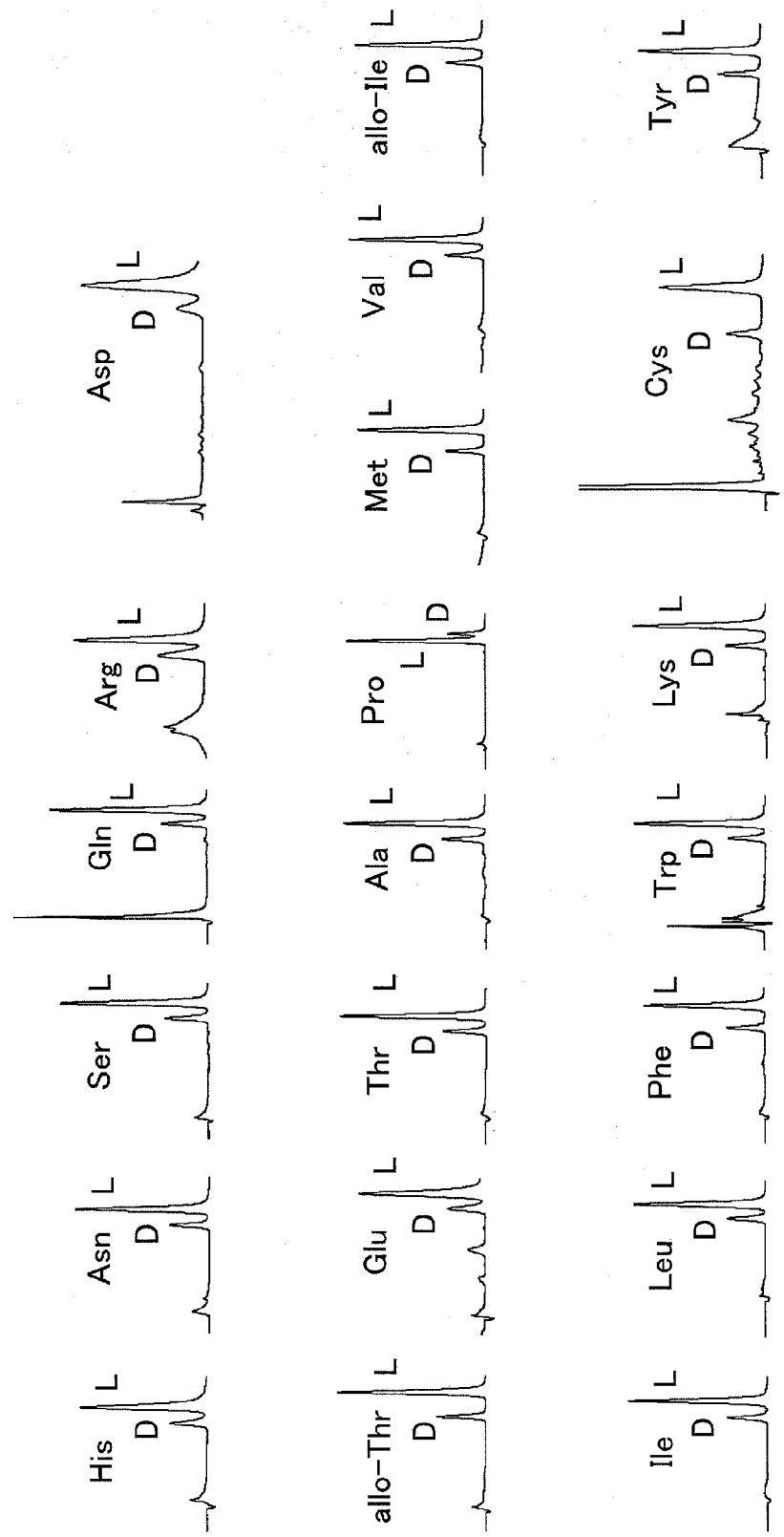
[FIG. 3] is chromatograms of amino acids in Comparative Example 1.

FIG. 3 illustrates chromatograms of amino acids.

It was found from FIG. 3 that the L-body of proline (Pro) was eluted earlier than the D-body thereof whereas the D-bodies of the amino acids other than proline (Pro) were eluted earlier than the L-bodies thereof.

Furthermore, it was found that resolutions of peaks originating from the D-bodies and peaks originating from the L-bodies were high with respect to all the amino acids because peak-to-valley ratios thereof were greater than or equal to 2.0 and symmetry coefficients thereof were less than 4.0.

Comparative Example 2

Mixtures of the D-bodies and the L-bodies of amino acids at mass ratios of 1:4 were separated similarly to Practical Example 1 expect that SUMICHIRAL (registered trademark) OA-3100S (produced by SCAS, Ltd.) was used as a column. Here, an optically active component of SUMICHIRAL (registered trademark) OA-3100S (produced by SCAS, Ltd.) was (S)-valine.

Figure 4:
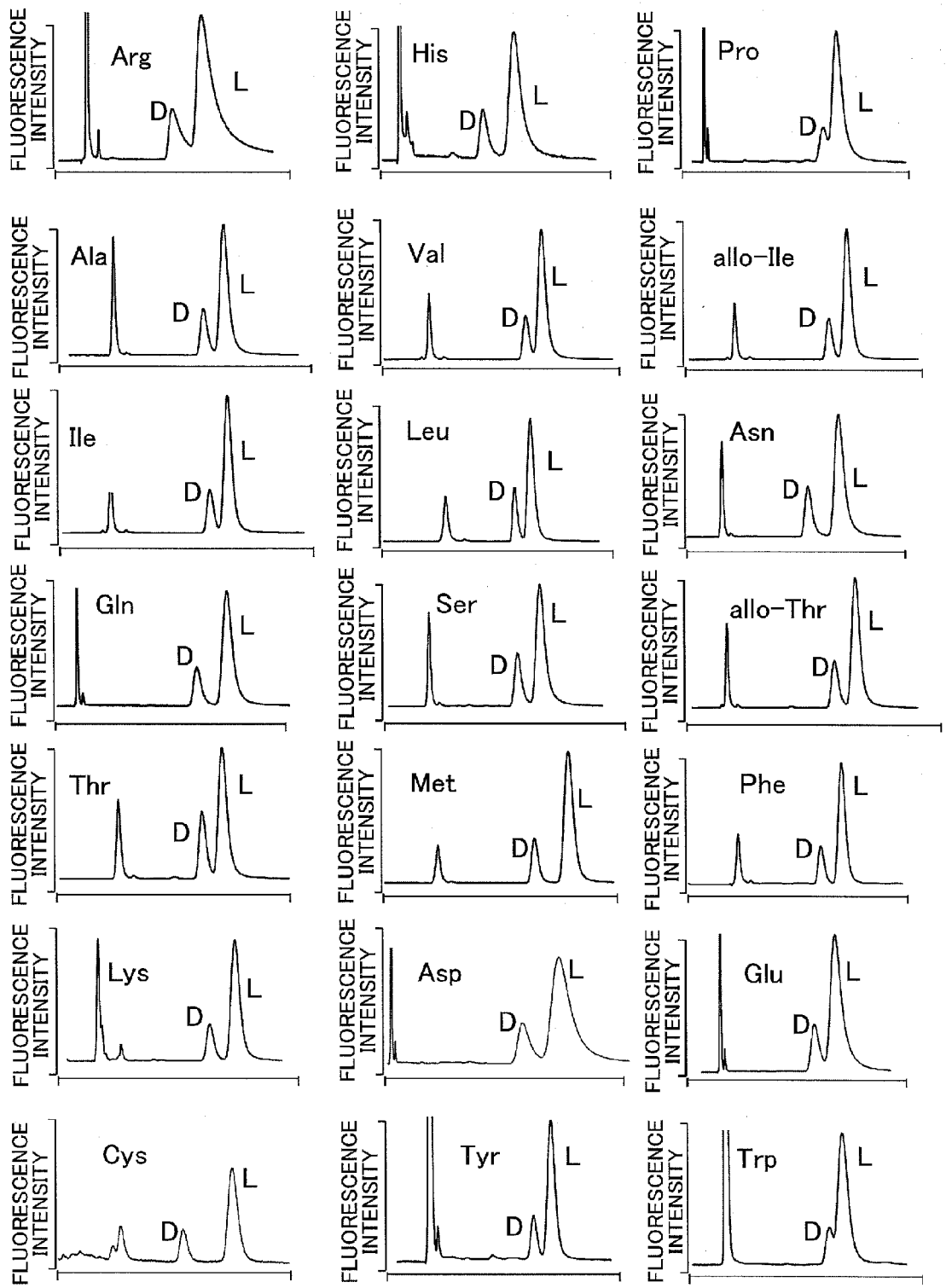
[FIG. 4] is chromatograms of amino acids in Comparative Example 2.

FIG. 4 illustrates chromatograms of amino acids.

It was found from FIG. 4 that the D-bodies of all the amino acids were eluted earlier than the L-bodies thereof.

Furthermore, a peak-to-valley ratio of proline (Pro) was 1.6 and a peak-to-valley ratio of tryptophan (Trp) was 1.3 whereas peak-to-valley ratios of the amino acids other than proline (Pro) and tryptophan (Trp) was greater than or equal to 2.0. On the other hand, a symmetry coefficient of arginine (Arg) was 5.9 and a symmetry coefficient of histidine (His) was 4.0 whereas symmetry coefficients of the amino acids other than arginine (Arg) and histidine (His) were less than 4.0. Hence, it was found that resolutions of peaks originating from the D-bodies of proline (Pro), tryptophan (Trp), arginine (Arg), and histidine (His) and peaks originating from the D-bodies thereof were low.

Here, as a compound represented by chemical formula (4) instead of the compound represented by chemical formula (3) in Practical Example 1 was used to fabricate a filler, the L-bodies of all the amino acids were eluted earlier than the D-bodies thereof.

[Appendix]

Embodiment (1) is a separating agent characterized in that a group represented by a chemical formula of:

[Chem. 1]

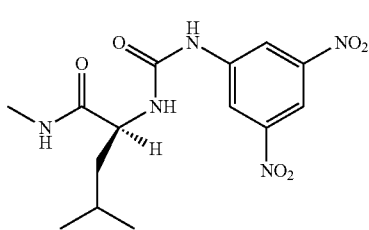

(1)

or a group represented by a chemical formula of:

[Chem. 2]

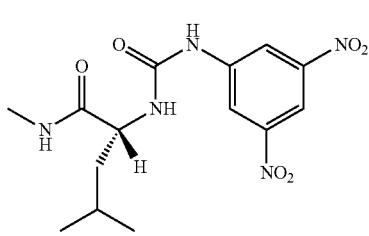

(2)

is introduced on a surface thereof.

Embodiment (2) is a manufacturing method of a separating agent characterized by having a step of condensing a compound represented by a chemical formula of:

[Chem. 3]

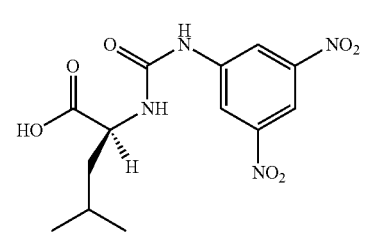

(3)

or a compound represented by a chemical formula of:

[Chem. 4]

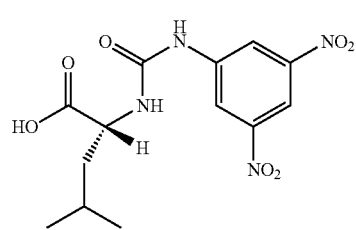

(4)

with a substrate with an amino group being present on a surface thereof.

Embodiment (3) is a separating agent characterized by being manufactured by the manufacturing method of a separating agent as described in Embodiment (2).

Embodiment (4) is a column characterized by having the separating agent as described in Embodiment (1) or (3).

Embodiment (5) is a liquid chromatograph characterized by having the column as described in Embodiment (4), Embodiment (6) is a separation method characterized by having a step of separating an enantiomer or a dias iereomer by using the column as described in Embodiment (4).

Embodiment (7) is a compound characterized by being represented by a chemical formula of:

[Chem. 5]

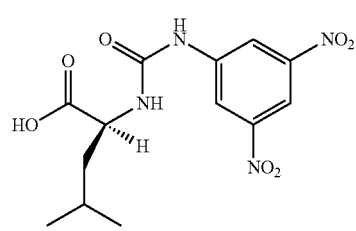

(3)

or a chemical formula of:

[Chem. 6]

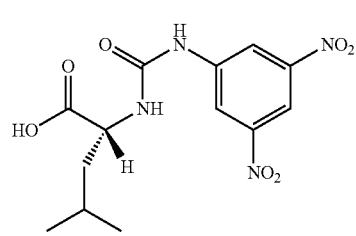

(4)

The present international application claims priority based on Japanese Patent Application No. 2012-018838 filed on Jan. 31, 2012 and an entire content of Japanese Patent Application No. 2012-018838 is incorporated by reference in the present international application.

The invention claimed is:
1. A separating agent comprising:
a substrate; and
a group of a following chemical formula:

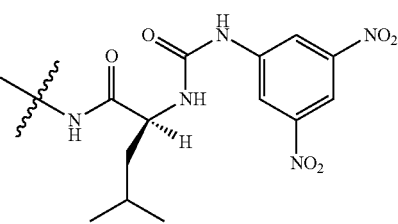

(1)

or a group of a following chemical formula:

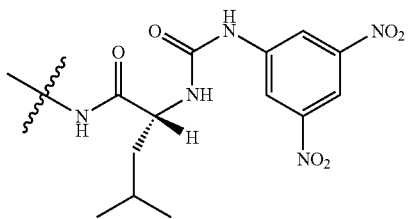
(2)

attached on a surface of the substrate.

2. A manufacturing method of a separating agent comprising a step of condensing a compound of a following chemical formula:

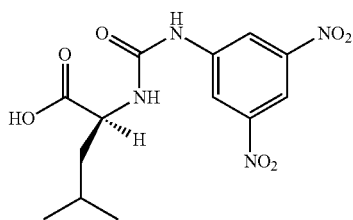
(3)

or a compound of a following chemical formula:

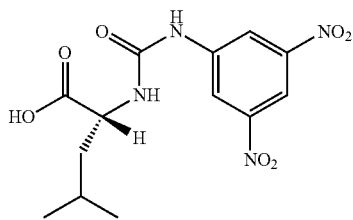
(4)

with a substrate with an amino group being present on a surface thereof.

3. A separating agent manufactured by the manufacturing method of a separating agent as claimed in claim 2.

4. A column comprising the separating agent as claimed in claim 1.

5. A liquid chromatograph comprising the column as claimed in claim 4.

6. A separation method comprising a step of separating a pair of enantiomers or a set of diastereomers by using the column as claimed in claim 4.

7. A compound of a following chemical formula:

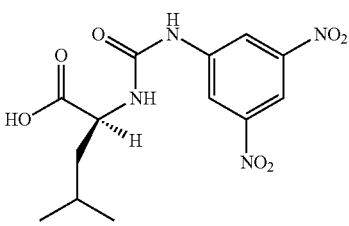
(3)

or a following chemical formula:

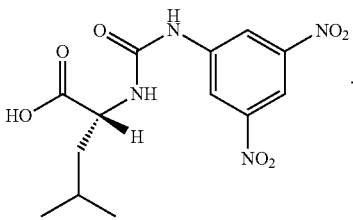
(4)

* * * * *